(12) United States Patent
Tucker et al.

(10) Patent No.: US 8,252,033 B2
(45) Date of Patent: Aug. 28, 2012

(54) PHOTOTHERAPY APPARATUS FOR SKIN TREATMENT

(75) Inventors: Gavin Tucker, Irvine, CA (US); Nicholas Brox, Laguna Beach, CA (US); Jeffrey Braile, Boca Raton, FL (US); Morgan Pepitone, Newport Beach, CA (US)

(73) Assignee: Apira Science, Inc., Irvine, CA (US)

( * ) Notice: Subject to any disclaimer, the term of this patent is extended or adjusted under 35 U.S.C. 154(b) by 0 days.

(21) Appl. No.: 13/446,325

(22) Filed: Apr. 13, 2012

(65) Prior Publication Data

US 2012/0197359 A1    Aug. 2, 2012

Related U.S. Application Data

(60) Division of application No. 12/807,911, filed on Sep. 16, 2010, now Pat. No. 8,192,473, which is a continuation-in-part of application No. 12/586,290, filed on Sep. 18, 2009, now abandoned.

(60) Provisional application No. 61/211,630, filed on Apr. 1, 2009, provisional application No. 61/136,630, filed on Sep. 19, 2008.

(51) Int. Cl.
*A61N 5/06* (2006.01)

(52) U.S. Cl. .................................. 607/91; 606/9; 607/90
(58) Field of Classification Search ... 606/9; 607/88–94
See application file for complete search history.

(56) References Cited

U.S. PATENT DOCUMENTS

| | | | |
|---|---|---|---|
| 2004/0153131 A1* | 8/2004 | Yorke | 607/91 |
| 2008/0077199 A1* | 3/2008 | Shefi et al. | 607/88 |
| 2009/0012586 A1* | 1/2009 | Kepecs | 607/89 |

FOREIGN PATENT DOCUMENTS

WO    WO 2004026400 A1 *    4/2004

* cited by examiner

*Primary Examiner* — Henry M Johnson, III
(74) *Attorney, Agent, or Firm* — Robert M. Downey, P.A.

(57) ABSTRACT

A wearable hands-free apparatus for providing phototherapy treatment to a number of skin related conditions includes a head unit (e.g., a headset, headphones, headband, or helmet unit) with earphones to allow the user to listen to an audio program during a treatment. The head unit supports a light emitting canopy band that is fitted with an array of light generating sources, such as light emitting diodes (LEDs), laser diodes, or infrared lights, that emit light within a particular wavelength range correlating with the treatment of one or more specific skin-related conditions. The light emitting canopy band is specifically designed for providing complete, uniform and consistent light coverage to a user's face.

17 Claims, 7 Drawing Sheets

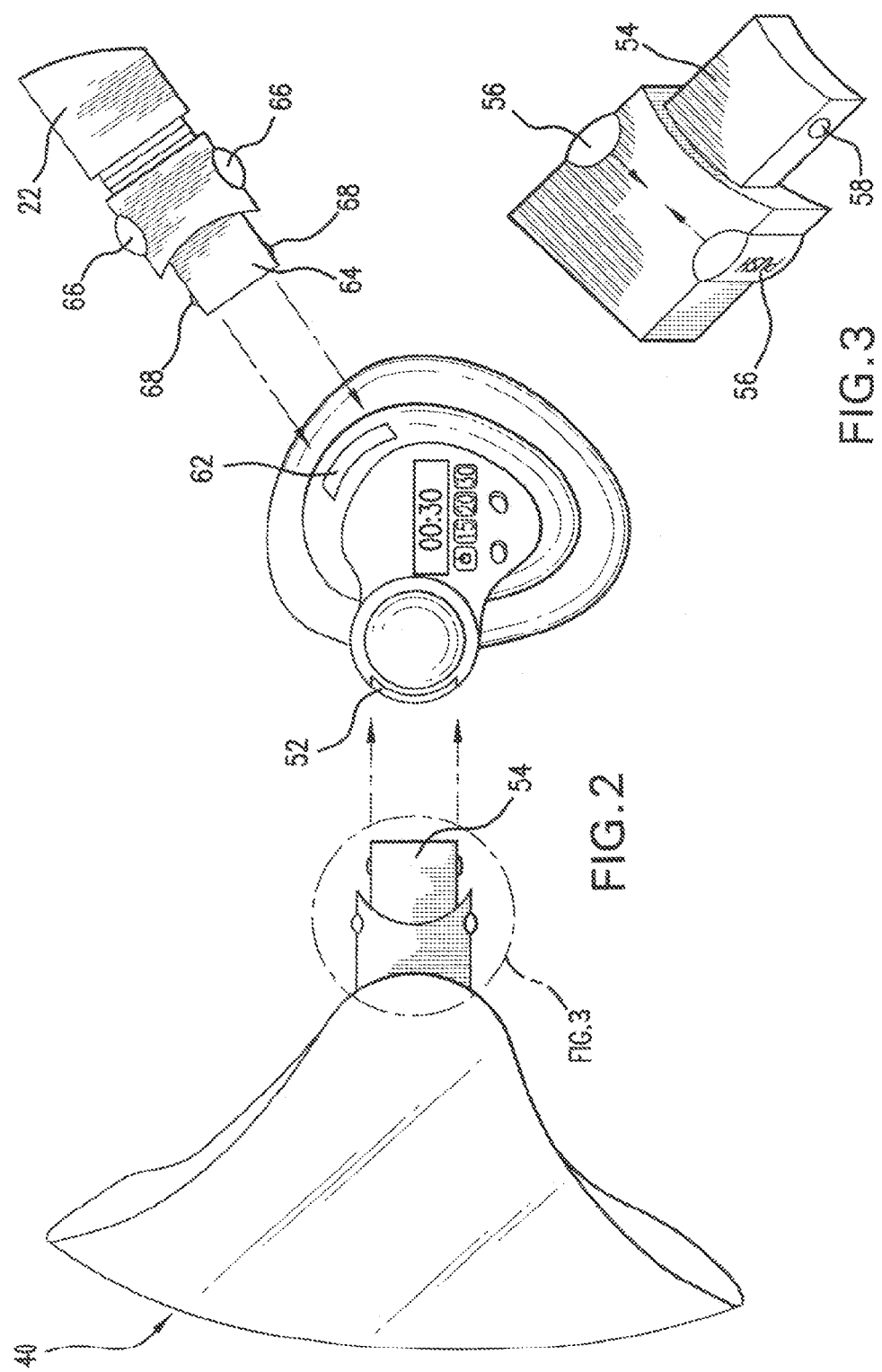

PHOTOTHERAPY APPARATUS FOR SKIN TREATMENT

This application is a Divisional Application of co-pending application Ser. No. 12/807,911 filed Sep. 16, 2010, which is a Continuation-In-Part (CIP) of U.S. non-provisional patent application Ser. No. 12/586,290 filed on Sep. 18, 2009, which is based on provisional patent application Ser. No. 61/136,630 filed on Sep. 19, 2008 and provisional patent application Ser. No. 61/211,630 filed on Apr. 1, 2009.

BACKGROUND OF THE INVENTION

1. Field of the Invention

This invention relates to light therapy for the treatment of skin and, more particularly, to a phototherapy apparatus that includes a head canopy band having light generating sources and audio headphones, and wherein the device is capable of providing hands-free therapeutic aid to a user's skin by way of evenly distributed light of various beneficial wavelengths that is directed onto particular treatment areas of a user's skin.

2. Discussion of the Related Art

People are frequently confronted with a variety of different skin-related conditions, such as acne, sun spots, wrinkling of the skin, psoriasis and non-melanoma skin cancer. In response, an assortment of treatment products, each typically targeting one specific skin-related condition, have been developed over the past 75 years and made available to the public. Many of these products are in the form of a topical solution that requires an arduous application process.

More recently, the use of phototherapy to treat various skin conditions has become increasingly popular. Phototherapy consists of exposure to specific wavelengths of light using lasers, light emitting diodes (LED's) (both individual and arrays), IPL's (Intense Pulsed Light) and other light sources, for a prescribed amount of time to both treat disease and affect cosmetic enhancements to the skin. The use of phototherapy in medical science and aesthetics is rapidly evolving as more and more wavelengths of light are being identified to target various sections of cells in order to stimulate cellular proficiency and enhance the body's ability to heal and rejuvenate itself. Phototherapy is currently used to treat acne, wrinkles, sun and age spots, rosacia, eczema, and wound healing through wavelengths indicated by various colors (i.e., wavelengths) of the light spectrum. By utilizing various wavelengths, colors relatively close on the spectrum can cause different effects when applied to various parts on the body.

For example, red light at a wavelength between 650 and 670 nanometers has been clinically shown to cause increased melanin production and protein synthesis. Red and infrared lights have also been used to increase the production of collagen and to reduce redness, dilated capillaries and damage to the skin, as well as reduction of wrinkles and fine lines. Blue light has been clinically shown to reduce acne and, when combined with red light, eliminates acne and reduces the scarring often associated with acne treatment. Yellow and Amber lights have been clinically shown to reduce fine lines and wrinkles, rosacia, and can help to repair sun damaged skin. Green light has been shown to reduce and eliminate sun and age spots, lighten freckles and also help promote more luminous skin condition and overall radiance of the skin. As set forth above, many of these light sources have multiple benefits, cross over each other in treating certain ailments and work to promote a variety of benefits to the skin. These light sources are often used in combinations to provide increased efficacy and various degrees of stimulation.

Science throughout the years has determined the effects of various wavelengths of light, but absorption is the key to cellular change. Light therapy emits photons which are absorbed by the skins photoreceptors. Skin cells respond well to phototherapy involving low level light due to the fact that cells reside just underneath the skin surface, making these low levels of energy able to reach the receptor sites and induce photochemistry.

There are a number of phototherapy devices currently available for home use to treat skin conditions. The majority of these are hand held devices, varying in both size and number of light sources (i.e., laser diodes, LED's, or infrared diodes). These devices are manually moved around the face by the user and require a constant movement in order to expose the entire surface area to the light sources. This results in an uneven treatment protocol, as the average user is unlikely to be able to cover the entire surface area through manual movements and will leave certain areas untreated. Further, due to the need for a manageable size (must fit in the hand), these devices are often underpowered.

Several phototherapy devices have been developed that are adapted to be portably worn by a user in a hands-free mode of operation. For example, U.S. Pat. App. Pub. No. 2006/0030908 to Powell et al. discloses a skin treatment phototherapy device that may comprise a clamshell structure, pen shape, facial mask, or desk lamp design, and which includes multi-colored LEDs. The Powell device attempts to treat a variety of skin conditions on the face and other skin regions below the user's head. Depending on the skin condition to be treated, the corresponding wavelengths, intensity levels, and time interval for the skin treatment can be varied by a control system. However, this device lacks a suitable structure and design for directing an evenly distributed light pattern.

The present invention provides the home use equivalent of a clinical stationary laser phototherapy system in a convenient and easy to use device. Moreover, the present invention provides the added benefit of ensuring a uniformly consistent distance from each of the light emitting sources to the skin.

The present invention seeks to address the limitations and shortcomings of the above described phototherapy treatment devices, by providing a canopy band having an array of light emitting sources optimally positioned for application of light from the array of light emitting sources to the face of the user. The phototherapy device is designed to maximize the efficiency of a variety of skin treatments through use of either fixed or removable canopy bands or plates that are fitted with an array of light emitting sources.

SUMMARY OF THE INVENTION

The present invention is directed to a wearable hands-free apparatus that provides phototherapy to the skin tissue and layers of a user's dermis. The phototherapy apparatus utilizes an array of light generating sources, which are housed within a unique canopy band or face plate that is structured and configured to provide complete and evenly distributed light to the entire face area being treated. For this application, the phrase "light generating sources" includes, but is not limited to, light emitting diodes (LEDs), laser diodes, infrared, and intense pulse lights (IPLs). The photo-biostimulation process achieved by use of the phototherapy apparatus of this invention produces an increase in ATP and keratin production, enhancement in blood flow and circulation, as well as an increase in collagen production. As previously noted, phototherapy can be used to treat a number of skin conditions, such as acne, sunspots, wrinkle reduction, skin tightening, psoriasis, eczema and collagen production.

Each form of treatment requires light emitted within a particular wavelength range in order to be sufficiently absorbed into the skin tissue, to thereby treat a user's particular skin-related condition. The canopy band or plate houses an array of light generating sources that are capable of emitting light within a range of output wavelengths in order to provide one or more penetration depths and photo-biostimulation effects. In a further embodiment of the invention, each canopy band may contain an array of mixed light generating sources, wherein certain light generating sources emit light within one wavelength range, while other light generating sources emit light within different wavelength ranges, thereby targeting different areas of the cell.

The canopy band may be fixed as an integral part of the head unit or, alternatively, may be interchangeably attached by way of a releasable securing mechanism. Various embodiments of the releasable securing mechanism utilizing different methods of interchangeable attachment are contemplated.

The light generating sources (e.g., diodes) may be adapted to pulse according to a proprietary algorithm that is programmed in the memory of a control device. The algorithm may provide for pulsed light in specific pre-determined patterns and timing sequences in accordance with a particular skin related treatment.

BRIEF DESCRIPTION OF THE DRAWINGS

For a fuller understanding of the nature of the present invention, reference should be made to the following detailed description taken in conjunction with the accompanying drawings in which:

FIG. 2 is an exploded side elevational view of the embodiment of FIG. 1 showing the phototherapy apparatus of the present invention, in accordance with a preferred embodiment, as it is when dismantled into separate parts, and including a canopy band or plate with an array of light generating sources, a set of headphones, and a head support band;

FIG. 3 is an isolated view of the male component taken from FIG. 2, including two release buttons, and a releasing mechanism;

Like reference numerals refer to like referenced parts throughout the several views of the drawings.

DETAILED DESCRIPTION OF THE PREFERRED EMBODIMENTS

Figure 1:
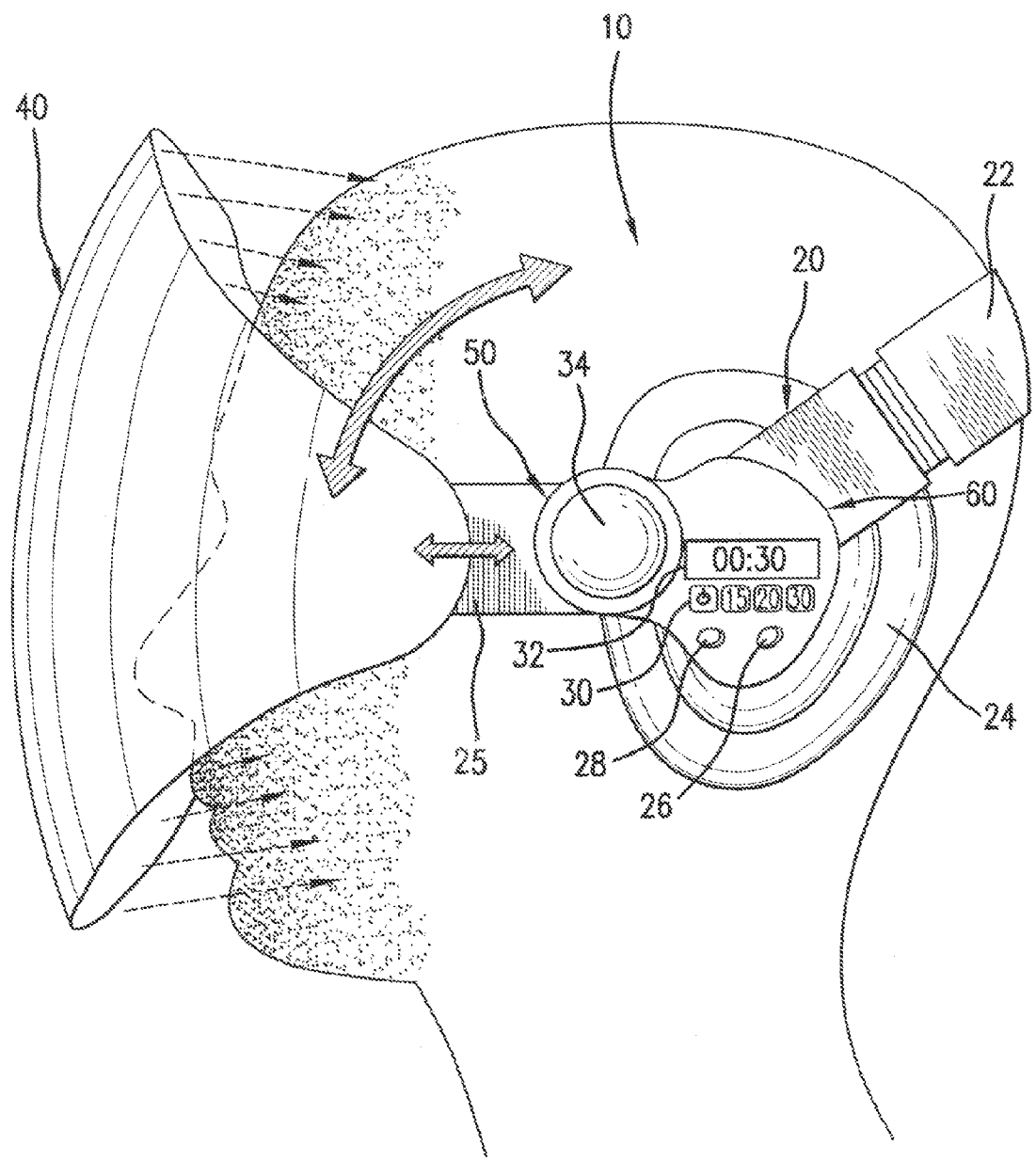
FIG. 1 is a side profile view showing the phototherapy apparatus of the present invention, in accordance with one embodiment, and including a canopy band or plate with an array of light generating sources emitting light within a range of wavelengths, which is positioned in spaced, opposing relation to the user's face, a headset unit, an interchangeable point for attaching or detaching canopy bands, a set of headphones, a set of controls for controlling the operations of the apparatus, an LCD timer and function display system, an input for a rechargeable battery system, and an audio input.

Referring to the several views of the drawings, the wearable hands-free apparatus that provides phototherapy treatment to the skin tissue and layers of a user's dermis is shown according to several embodiments of the invention and is generally indicated as 10. The phototherapy apparatus 10 is specifically sized, structured and configured to be worn on a person's head.

In each of the embodiments of the invention, the phototherapy apparatus 10 includes a head unit 12 (e.g., a headset, head phones, headband, or helmet) with left and right audio earphones 24 to allow the user to listen to an audio program during a phototherapy treatment. The head unit 12 supports a light emitting canopy band or plate 40 that houses an array of light generating sources 102 (see FIGS. 6 and 7), such as light emitting diodes (LEDs), lasers, infrared lights, or other suitable light sources that are adapted to emit light within a particular wavelength range correlating with the treatment of one or more skin-related conditions.

The left and right audio headphones 24 are adjustably supported on slidable arm members 25 that extend from the head unit 12 at the bottom ends of downwardly extending portions on the left and right sides of the head unit 12.

The embodiment shown in FIGS. 1-3 provides for interchangeable canopy bands or plates. Each interchangeable canopy band 40 removably attaches to a supporting head unit that is meant to be worn on a user's head. In the embodiment shown in FIG. 1, the head unit is a headset unit 20. The canopy band 40 is supported by the headset unit such that light is directly emitted toward the user's face. The headset unit 20 includes a detachable, adjustable head support band 22, which can be adjusted for snuggly fitting on the user's head and is necessary to prevent the headphones from slipping. The headset unit 20 further includes two audio headphones 24 on opposite sides of the adjustable head support band 22, which are adapted to come in contact with the user's ears when the phototherapy apparatus 10 is properly worn on the user's head. An audio input 28 is located on the headset unit 20 and communicates with the two audio headphones 24, allowing the user to listen to an audio feed from any general audio device, such as an MP3 player (e.g., an iPod). An LCD timer and function display system 32 is located on the headset unit 20, which displays a countdown timer and user functions, such as output wavelength. An input for a rechargeable battery system 26 is also located on the headset unit 20.

As illustrated in FIG. 1, there is a pivot mechanism 34 connected to the headphones 24, which allows for rotational movement of the canopy band 40 relative to the user's head, and consequently, complete facial coverage by the canopy band 40.

As shown in FIGS. 2 and 3, on each side of the headset unit 20 is a female component 52 of a releasable securing mechanism 50. On opposite sides of each canopy band 40 is a male component 54 of the releasable securing mechanism 50. Each male component 54 has a release button 56 and a release mechanism 58. In operation, the male component 54 snaps into the female component 52 and securely fixes the canopy band 40 with the headset unit 20. In order to separate the canopy band 40 from the headset unit 20, the user must squeeze together the opposite ends of the release button 56, which will unhinge the release mechanism 58 and allow separation of the male component 54 from the female component 52.

Further illustrated in FIGS. 2 and 3 is the head support band securing mechanism 60, which helps support the phototherapy apparatus 10 upon the user's head when required. The head support band securing mechanism 60 is comprised of dual female components 62 that are located on the headphones 24, and duel male components 64 that are located on the head support band 22. In operation, the male component 64 snaps into the female component 62 and securely fixes the headphones 24 with the head support band 22. In order to separate the headphones 24 from the head support band 22, the user must squeeze together the opposite ends of the release button 66, which will unhinge the release mechanism 68 and allow separation of the male component 64 from the female component 62.

Figure 4:
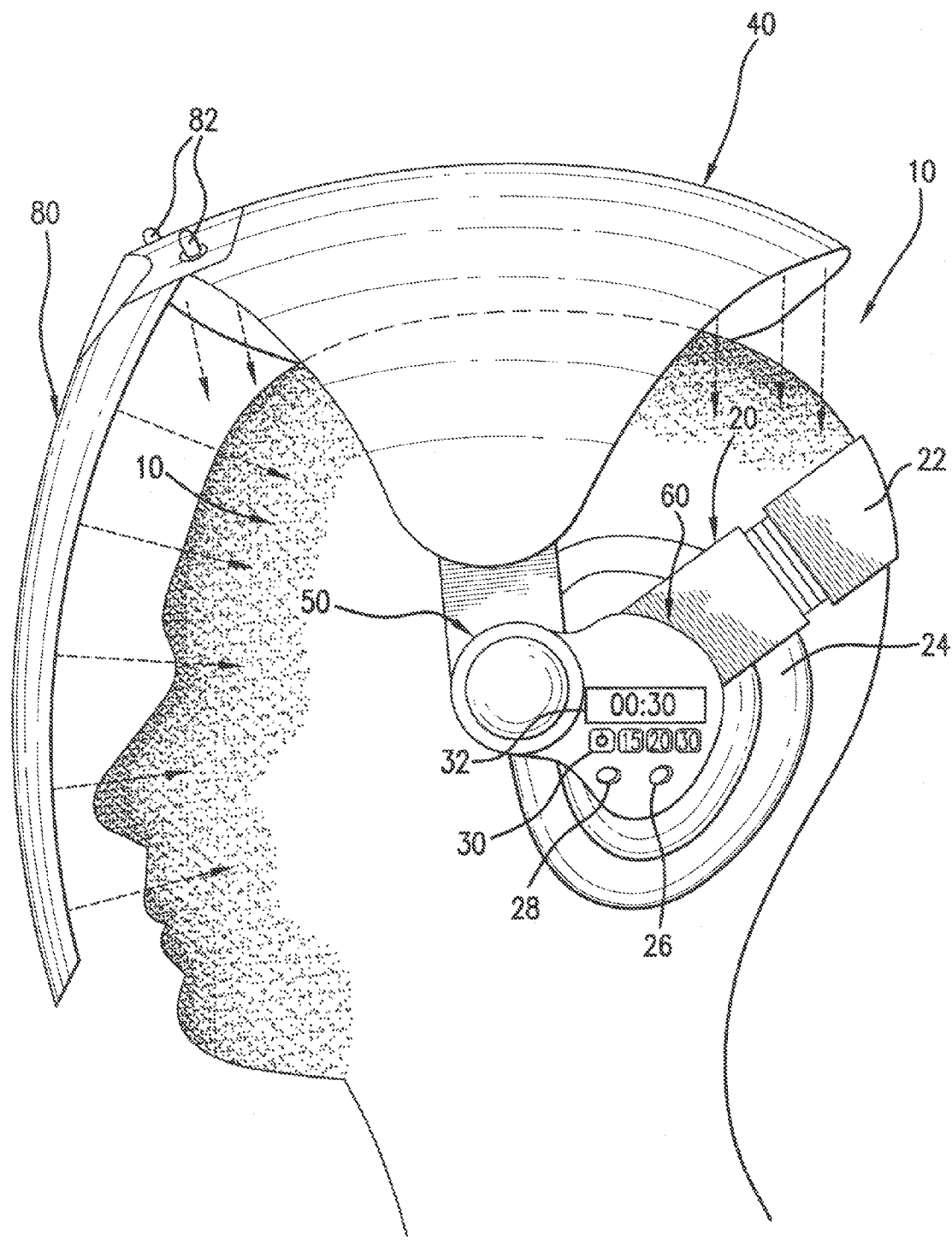
FIG. 4 is a side profile view showing the phototherapy apparatus of the present invention, in accordance yet a further embodiment, and including a fixed or detachable face plate with an array of light generating sources, which is positioned in spaced, opposing relation to the user's face, a canopy band with an array of light generating sources emitting light within a range of wavelengths, which is positioned in spaced, opposing relation to the user's scalp, a faceplate fastening mechanism, a headset unit, an interchangeable point for attaching or detaching canopy bands, a set of headphones, a set of controls for controlling the operations of the apparatus, an LCD timer and function display system, an input for a rechargeable battery system, and an audio input.

As illustrated in FIG. 4, the addition of a fixed or detachable face plate 80 connected to the canopy band 40 provides for a further embodiment of the phototherapy apparatus 10. The fixed or detachable face plate 80 houses an array of light generating sources 102 on its inner facing side, designed for providing evenly distributed phototherapy treatment to the user's face. This embodiment allows the user the option of treating both the scalp and face regions of the user's head, as the canopy band 40 in this embodiment is positionable in spaced, opposing relation to the user's scalp. There is a headband proprietary pivot point 74, which allows for rotational movement of the canopy band 40 relative to the user's head, and consequently, complete scalp and facial coverage by the canopy band 40.

Figure 5:
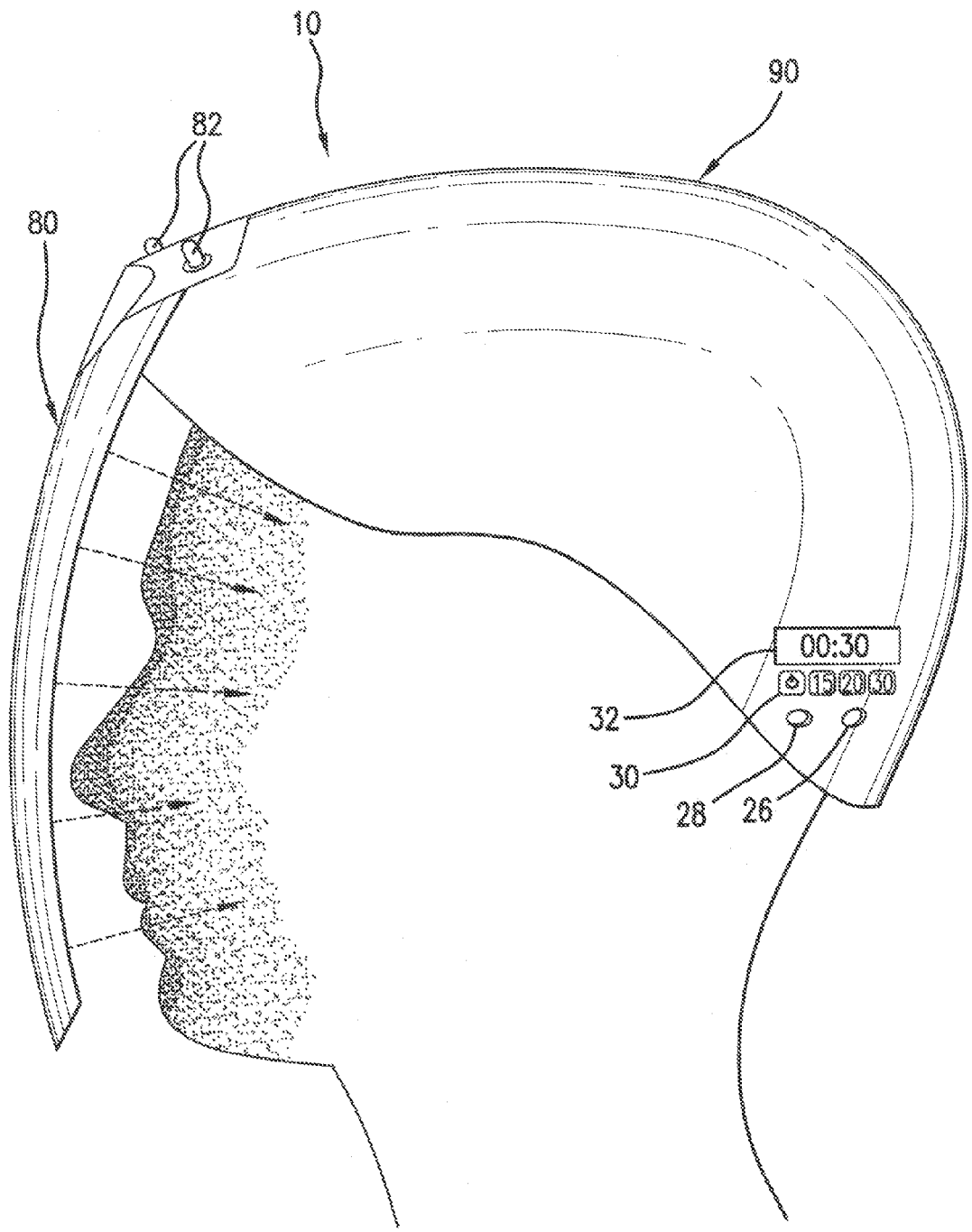
FIG. 5 is a side profile view showing the phototherapy apparatus of the present invention, in accordance with a further embodiment, and including a fixed or detachable face plate with an array of light generating sources, which is positioned in spaced, opposing relation to the user's face, a faceplate fastening mechanism, a helmet unit, a set of controls for controlling the operations of the apparatus, an LCD timer and function display system, an input for a rechargeable battery system, and an audio input.

Another embodiment of the phototherapy apparatus 10 is shown in FIG. 5, which illustrates a helmet unit 90 adapted to be worn on a user's head. Attached to the helmet unit 90 is a fixed or detachable face plate 80, which houses an array of light generating sources 102 on its inner facing side, designed for providing evenly distributed phototherapy treatment to the user's face.

Figure 6:
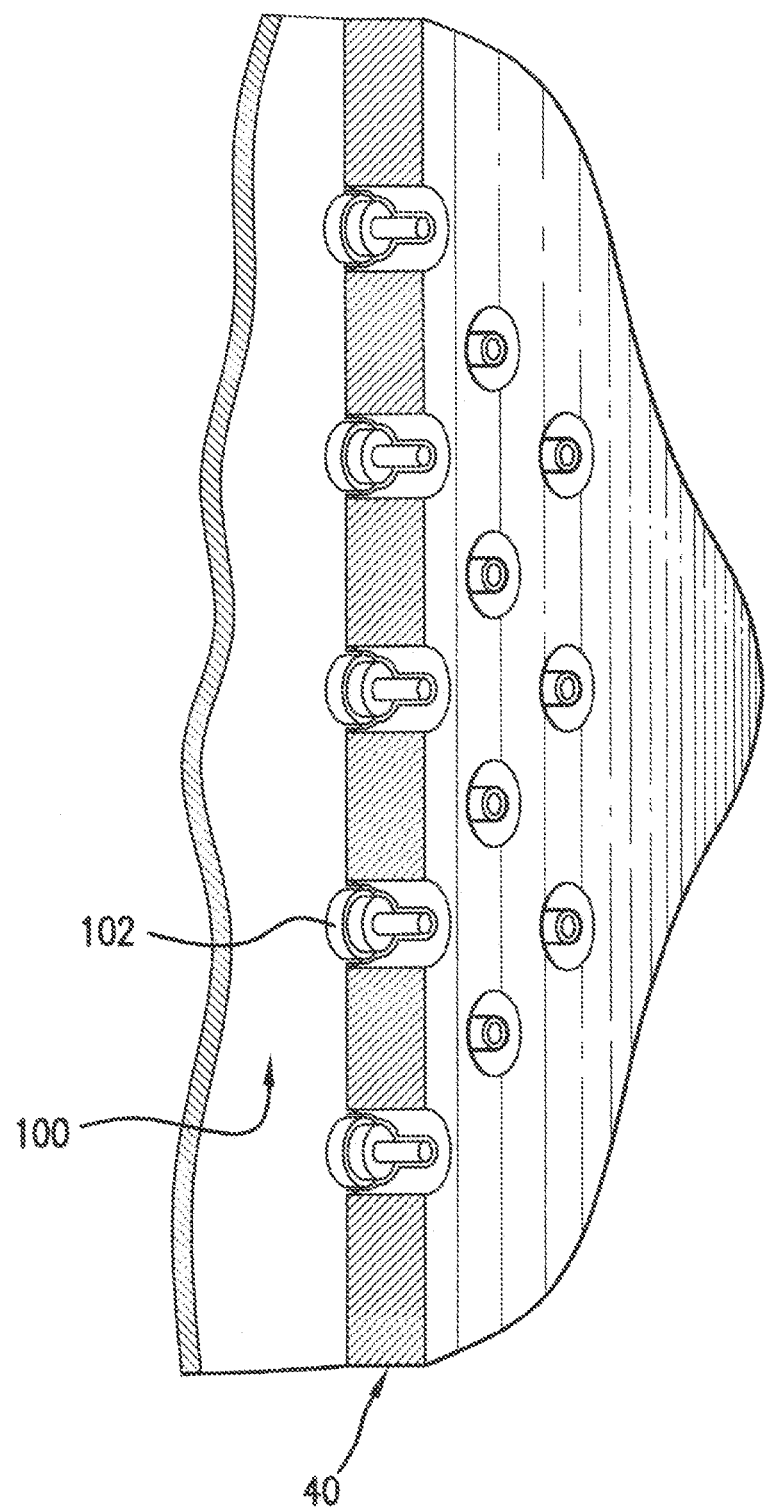
FIG. 6 is an isolated inner view of the canopy band or plate comprising an array of light generating sources mounted on the inner facing side of the canopy band or plate, showing the light consistency widening as it leaves the light generating source's aperture, as well as the resulting overlap of light on skin surface.
Figure 7:
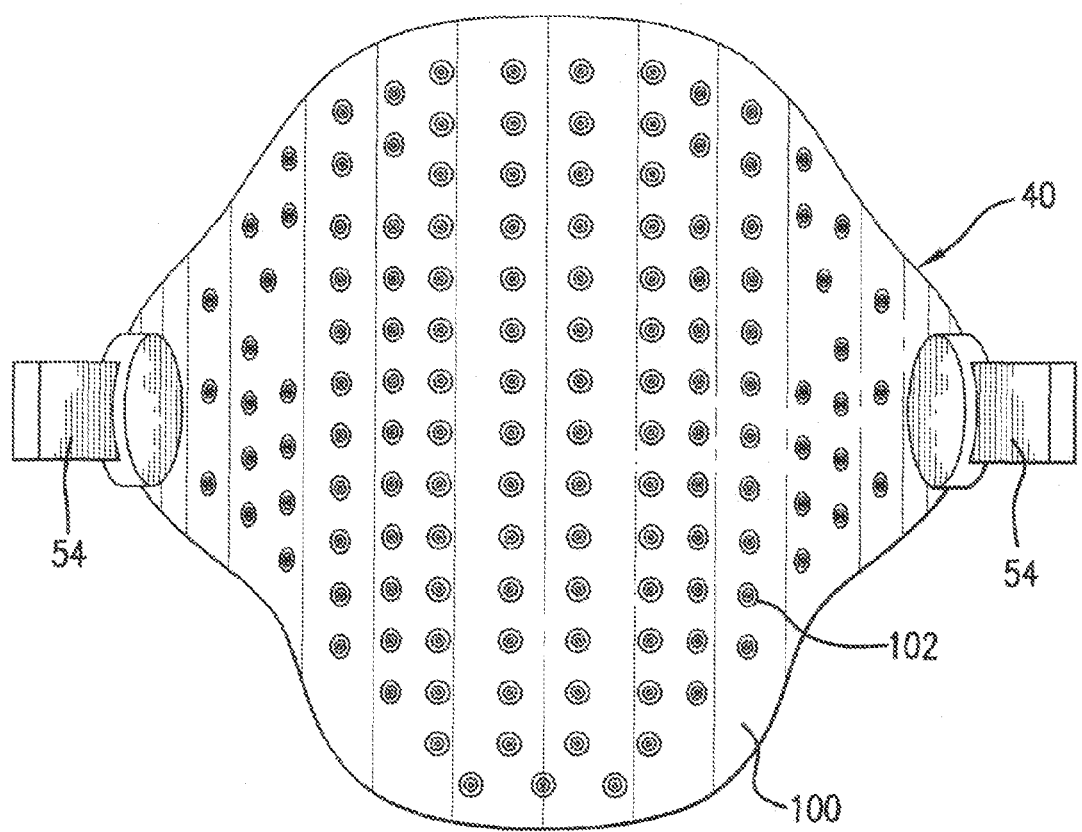
FIG. 7 is an isolated view of the inner facing side of a canopy band or plate, showing the array of light generating sources and the male component of the releasing mechanism.

As illustrated in FIGS. 6 and 7, an array of light generating sources 102 are mounted on the inner facing side 100 of a canopy band 40 that is positionable in spaced, opposing relation to a select area of the user's head. As an alternative to the array of light generating sources 102 being mounted on the inner facing side 100 of the canopy band 40, the array of light generating sources 102 can be snapped into place on the inner facing side 100 of the canopy band 40. In a further embodiment, the array of light generating sources 102 are composed of multiple wavelength light generating sources 102 within a single canopy band 40, wherein certain light generating sources 102 emit light within one particular wavelength range, while other light generating sources 102 emit light within different wavelength ranges. The spread of light from each light generating source 102 widens as it leaves the aperture, creating an overlap that provides a uniform distribution and intensity of light with enhanced penetration depth control to regions of skin tissue on the user's head. Additionally, protective eye wear can be worn by the user when the phototherapy apparatus 10 is being used to treat particular skin-related conditions on the face.

Figure 8:
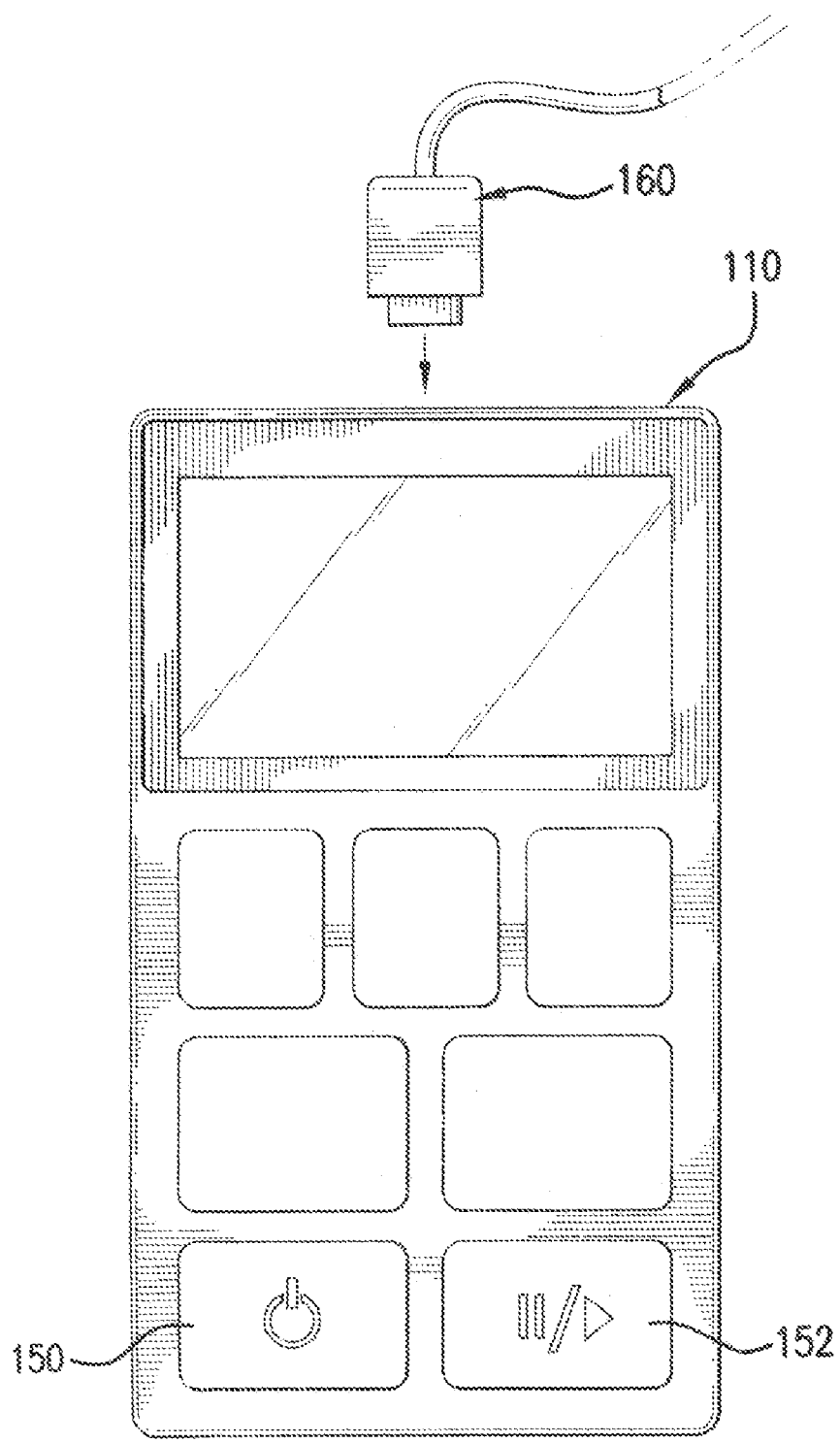
FIG. 8 is a top plan view of a hand held control unit that connects to the phototherapy apparatus.

Referring to FIG. 8, the hand held control unit 110 for operating the phototherapy apparatus 10 is shown and includes an on/off button 150 and a start/pause button 152. The hand held control unit 110 connects to the head unit 12 by a wire 160 that extends from the hand held unit 110 and plugs into the head unit 12 at a designated port. The hand held unit stores all programmed functions of the phototherapy apparatus in memory including operational functions of the array of light generating sources 102, as well as all audio functions connected with the headphones 24 on the head unit 12. The hand held control unit 110 provides for selection of audio programs stored in memory, as well as volume and other audio functions.

In each of the embodiments shown, depending on the type of condition being treated, light emitted at a particular output wavelength range is required to sufficiently penetrate the skin tissue. For example, in treating inflammation, lesions, or canker sores, a range (628 nm-694 nm) of red wavelengths is preferable; in treating rosacea or wrinkling of the skin, a range (568 nm-590 nm) of yellow wavelengths is preferable; in treating acne, a range (405 nm-476 nm) of blue wavelengths is preferable; in treating age spots, sun damage, or hyperpigmentation, a range (514 nm-543 nm) of green wavelengths is preferable; and in stimulating the skin to produce collagen and elastin, a range (700-1090 nm) of infrared wavelengths is preferable.

While the invention has been shown and described in accordance with several preferred and practical embodiments thereof, it is recognized that departures from the instant disclosure of the invention are fully contemplated within the spirit and scope of the invention and such changes, variations and modifications of the present invention are not to be limited except as recited in the following claims as interpreted under the Doctrine of Equivalents.

What is claimed is:

1. A wearable hands-free apparatus for providing phototherapy treatment to a user, said apparatus comprising:
    a head unit adapted to be worn on the user's head and including a pair of audio emitting earphones positionable on the user's ears and at least one canopy band;
    said at least one canopy band including an inner side that is positionable in spaced, opposing relation to the user's face when the head unit is worn on the user's head;
    an array of light generating sources on said inner side of said at least one canopy band and said array of light generating sources being positioned, structured and disposed for producing a light pattern that can be simultaneously directed onto the user's face, and each of said light generating sources being further structured and disposed for emitting light within a wavelength range according to a particular condition being treated by phototherapy using the apparatus;
    at least one control for controlling operation of each of the light generating sources in said array of light generating sources.

2. The apparatus as recited in claim 1 wherein said light generating sources are light emitting diodes (LEDs).

3. The apparatus as recited in claim 1 wherein said light generating sources are laser diodes.

4. The apparatus as recited in claim 1 wherein said light generating sources are intense pulse lights (IPLs).

5. The apparatus as recited in claim 1 wherein said light generating sources are infrared lights.

6. The apparatus as recited in claim 1 wherein said head unit includes an LCD timer and function display system.

7. The apparatus as recited in claim 6, further comprising a face plate structured and disposed for connecting to said head unit, and said face plate being further structured and disposed for housing a second array of the light generating sources for producing a light pattern that is directed onto the user's face.

8. The apparatus as recited in claim 1 wherein said at least one control includes an LCD display, and said at least one control further including a programmable memory for storing an algorithm that controls the timing and pulse rate of said array of light generating sources in accordance with a plurality of specific phototherapy treatments.

9. The apparatus as recited in claim 1 wherein said at least one control is a hand held device, and said hand held device including a programmable memory for storing an algorithm that controls the timing and pulse rate of said array of light generating sources in accordance with a plurality of specific phototherapy treatments.

10. A wearable hands-free apparatus for providing phototherapy treatment to a user's scalp and face, said apparatus comprising:
    a head unit adapted to be worn on the user's head and adapted to accept one of a plurality of canopy bands;
    a plurality of canopy bands each being removably attachable to said head unit and each including an inner side that is positionable between a first operable position and a second operable position, the first operable position defined by the inner side of any one of the plurality of canopy bands positioned and disposed in spaced opposing relation to the user's face and the second operable position defined by the inner side of any one of the plurality of canopy bands positioned and disposed in spaced, opposing relation to the user's scalp;
    a pivot point on said apparatus structured and disposed for allowing rotation of each said plurality of canopy bands between the first and second operable positions;
    an array of light generating sources on said inner side of each of said plurality of canopy bands and being structured and disposed for producing a light pattern that is directed onto the user's face when the canopy bands are in the first operable position and onto the entire area of the user's scalp when the canopy bands are in the second operable position, and each of said light generating sources being further structured and disposed for emitting light within a selected wavelength range according to a particular condition being treated by phototherapy;
    a first of said plurality of canopy bands having said array of light generating sources adapted for emitting light within the selected wavelength ranges of 405 nm-476 nm;
    a second of said plurality of canopy bands having said array of light generating sources adapted for emitting light within the selected wavelength ranges of 514 nm-543 nm;
    a third of said plurality of canopy bands having said array of light generating sources adapted for emitting light within the selected wavelength ranges of 568 nm-590 nm;
    a fourth of said plurality of canopy bands having said array of light generating sources adapted for emitting light within the selected wavelength ranges of 628 nm-694 nm;
    a fifth of said plurality of canopy bands having said array of light generating sources adapted for emitting light within the selected wavelength ranges of 700 nm-1090 nm; and
    at least one control for controlling operation of said array of light generating sources.

11. The apparatus as recited in claim 10 wherein said light generating sources are light emitting diodes (LEDs).

12. The apparatus as recited in claim 10 wherein said light generating sources are laser diodes.

13. The apparatus as recited in claim 10 wherein said light generating sources are intense pulse lights (IPLs).

14. The apparatus as recited in claim 10 wherein said head unit includes an LCD timer and function display system.

15. The apparatus as recited in claim 14, further comprising a face plate structured and disposed for connecting to said head unit, and said face plate being further structured and disposed for housing a second array of the light generating sources for producing a light pattern that is directed onto the user's face.

16. The apparatus as recited in claim 10 wherein said at least one control is a hand held device, and said hand held device including a programmable memory for storing an algorithm that controls the timing and pulse rate of said array of light generating sources in accordance with a plurality of specific phototherapy treatments.

17. The apparatus as recited in claim 10 wherein said at least one control includes an LCD display, and said at least one control further including a programmable memory for storing an algorithm that controls the timing and pulse rate of said array of light generating sources in accordance with a plurality of specific phototherapy treatments.

* * * * *